(12) United States Patent
Hickman et al.

(10) Patent No.: US 10,894,753 B1
(45) Date of Patent: Jan. 19, 2021

(54) PARAFFIN UTILIZATION OF LINEAR ALKYL BENZENE PRODUCTION

(71) Applicant: UOP LLC, Des Plaines, IL (US)

(72) Inventors: Amanda Hickman, Des Plaines, IL (US); Wei Pan, Hoffman Estates, IL (US); Stephen Sohn, Arlington Heights, IL (US); Phuong Thi Mai Do, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/818,085

(22) Filed: Mar. 13, 2020

(51) Int. Cl.
- *C07C 4/18* (2006.01)
- *C07C 309/30* (2006.01)
- *C07C 303/22* (2006.01)
- *C07C 15/04* (2006.01)

(52) U.S. Cl.
CPC ............... *C07C 4/18* (2013.01); *C07C 15/04* (2013.01); *C07C 303/22* (2013.01); *C07C 309/30* (2013.01); *C07C 2529/08* (2013.01)

(58) Field of Classification Search
CPC ......... C07C 15/08; C07C 2/66; C07C 5/2737; C07C 11/02; C07C 5/2775; C07C 5/2708; C07C 5/367; C07C 15/04; C07C 5/05; C07C 5/11; C07C 5/2732; C07C 5/277; C07C 5/327; C07C 5/3337; C07C 51/00; C07C 7/13; B01J 29/70; B01J 29/06; B01J 29/90; B01J 29/084; B01J 29/005; B01J 29/7007; B01J 29/85; B01J 19/0093; B01J 29/40; B01J 23/42; B01J 35/023; B01J 35/08; B01J 35/1061; B01J 37/10; B01J 21/12
See application file for complete search history.

(56) References Cited

U.S. PATENT DOCUMENTS

| | | | |
|---|---|---|---|
| 4,523,045 A | 6/1985 | Vora | |
| 5,196,574 A | 3/1993 | Kocal | |
| 5,300,715 A | 4/1994 | Vora | |
| 6,315,964 B1 | 11/2001 | Knifton et al. | |
| 6,617,481 B1 | 9/2003 | Kulprathipanja et al. | |
| 6,756,515 B2 * | 6/2004 | Rende | B01J 23/626 585/374 |
| 8,350,110 B2 * | 1/2013 | Sohn | C07C 4/14 585/470 |
| 9,212,108 B2 | 12/2015 | Sohn et al. | |

* cited by examiner

*Primary Examiner* — Sharon Pregler

(57) ABSTRACT

A process is provided for producing linear alkylbenzenes with an improved yield from paraffin feed due to the use of a new catalyst that has a reduced selectivity to produce undesired aromatic compounds. In some embodiments, it is now possible to operate the process without including a unit to remove such aromatic compounds which allows for an operator of a plant to make modifications to the process to increase product yield.

15 Claims, 4 Drawing Sheets

PARAFFIN UTILIZATION OF LINEAR ALKYL BENZENE PRODUCTION

FIELD OF THE INVENTION

The present invention relates to the production of monoalkylated aromatic compounds including linear alkyl benzene in particular, the present invention relates to the conversion of paraffins with a reduction in production of undesired aromatic compounds.

BACKGROUND

The alkylation of benzene with olefins produces a variety of alkylbenzene compounds that have various commercial uses. Examples include the alkylation of benzene with olefins having 8 to 16 carbons for the production intermediate compounds in the manufacture of detergents. The alkylbenzenes are sometimes referred to as phenylalkanes and are produced as a commodity in large scale facilities worldwide with production rates of between 50,000 and 200,000 metric tons per year. The alkylation process comprises reacting benzene with an olefin in the presence of a catalyst at elevated temperatures. The catalysts can be homogeneous or heterogeneous catalysts such as hydrogen fluoride, aluminum chloride, silica alumina, or zeolitic catalysts.

The desired alkylated compounds are monoalkylated aromatic compounds. Monoalkylated aromatic compounds include linear alkylbenzenes (LAB), which are used to form linear alkylbenzene sulfonates (LABS), a compound often used in the manufacture of detergents. Two common reactions for production of monoalkylated aromatic compounds are alkylation of aromatic compounds such as benzene and transalkylation of polyalkylated aromatic compounds.

Linear alkyl benzene is produced today from a C9-C14 linear paraffin stream that is first dehydrogenated to form mono-olefins and then passed to an alkylation catalyst with benzene. The dehydrogenation process results in a mixture of species including diolefins, triolefins, and aromatics. These species must then be removed via additional processing steps and at the expense of valuable parafin. The selectivity to these undesired side products increases at higher conversion with conventional catalysts. In particular, the aromatic species also attenuate the activity of solid acid alkylation catalysts. Due to the inherently lower alkylation selectivity to mono alkylated benzene by solid bed alkylation (SBA) vs hydrofluoric acid (HF) alkylation, it is unattractive for HF alkylation producers to switch to SBA because they must add in additional treatment steps and accept a lower paraffin utilization. A more efficient process has now been developed in which a reduced amount of aromatic compounds are produced in the dehydrogenation step.

SUMMARY OF THE INVENTION

A process is provided for producing monoalkylbenzenes comprising passing a C9-C14 paraffinic stream and a hereinafter derived paraffinic recycle stream to a dehydrogenation zone maintained at dehydrogenation conditions containing a dehydrogenation catalyst to produce an effluent stream comprising light hydrocarbon, hydrogen, feed paraffin hydrocarbons, the corresponding monoolefinic and diolefinic hydrocarbons to the feed paraffin hydrocarbons and C9-C14 alkylaromatics are produced. The effluent stream comprises less than 1.4 wt % of the C9-C14 alkylaromatics wherein the dehydrogenation zone catalyst comprises a layered catalyst composition comprising an inner core, an outer layer bonded to said inner core, the outer layer comprising delta and/or theta alumina and layer thickness less than about 100 microns having uniformly dispersed thereon at least one platinum group metal and at least one promoter metal; sending at least a portion of said effluent stream to a selective hydrogenation reactor to convert said diolefinic hydrocarbons to monoolefinic hydrocarbons and producing a treated effluent stream; sending said treated effluent stream to an alkylation zone; sending an aromatics stream comprising benzene to said alkylation zone operated at alkylation conditions to generate a process stream comprising paraffins, benzene, monoalkylbenzenes and heavy alkylbenzenes (HAB); separating the process stream, in a first separation unit, into a first stream comprising benzene, and a second stream comprising alkylbenzenes and paraffins; passing the second stream to a second separation unit to generate a third stream comprising paraffins, which is recycled back to the dehydrogenation zone, and a fourth stream comprising alkylbenzenes; passing the fourth stream to a third separation unit to generate a fifth stream comprising monoalkylated benzene, a sixth stream comprising heavy alkylbenzenes (HAB); passing the sixth stream to a fourth separation unit to generate a seventh stream comprising low-molecular weight HAB, and an eighth stream comprising high-molecular weight HAB; and optionally passing the eighth stream to a transalkylation zone; passing a benzene stream to the transalkylation zone operated at transalkylation conditions to generate a transalkylation effluent stream comprising monoalkylbenzenes; and passing the transalkylation effluent stream to the first separation unit.

In another embodiment, a process is provided for producing monoalkylbenzenes comprising passing a C9-C14 paraffinic stream and a hereinafter derived paraffinic recycle stream to a dehydrogenation zone maintained at dehydrogenation conditions containing a dehydrogenation catalyst to produce an effluent stream comprising light hydrocarbon, hydrogen, feed paraffin hydrocarbons, corresponding monoolefinic and diolefinic hydrocarbons to said feed paraffin hydrocarbons and C9-C14 alkylaromatics, wherein the effluent stream comprises less than 1.4 wt. % of said C9-C14 alkylaromatics wherein said dehydrogenation zone catalyst comprises a layered catalyst composition comprising an inner core, an outer layer bonded to the inner core, the outer layer comprising delta and/or theta alumina and layer thickness less than about 100 microns having uniformly dispersed thereon at least one platinum group metal and at least one promoter metal; sending at least a portion of said effluent stream to a selective hydrogenation reactor to convert said diolefinic hydrocarbons to monoolefinic hydrocarbons and producing a treated effluent stream; sending the treated effluent stream to an aromatics separation zone to remove at least a portion of said C9-C14 alkylaromatics and producing a treated effluent stream; sending the treated effluent stream to an alkylation zone; sending an aromatics stream comprising benzene to the alkylation zone operated at alkylation conditions to generate a process stream comprising paraffins, benzene, monoalkylbenzenes and heavy alkylbenzenes (HAB); separating the process stream, in a first separation unit, into a first stream comprising benzene, and a second stream comprising alkylbenzenes and paraffins; passing the second stream to a second separation unit to generate a third stream comprising paraffins, which is recycled back to the dehydrogenation zone, and a fourth stream comprising alkylbenzenes; passing the fourth stream to a third separation unit to generate a fifth stream comprising monoalkylated benzene, a sixth stream comprising heavy alkylbenzenes (HAB); passing the sixth stream to a fourth separation unit to generate a seventh stream comprising low-molecular weight HAB, and an eighth stream comprising high-molecular weight HAB; and optionally passing the eighth stream to a transalkylation zone; passing a benzene stream to the transalkylation zone operated at transalkylation conditions to generate a transalkylation effluent stream comprising monoalkylbenzenes; and passing the transalkylation effluent stream to the first separation unit.

DETAILED DESCRIPTION

Figure 1:
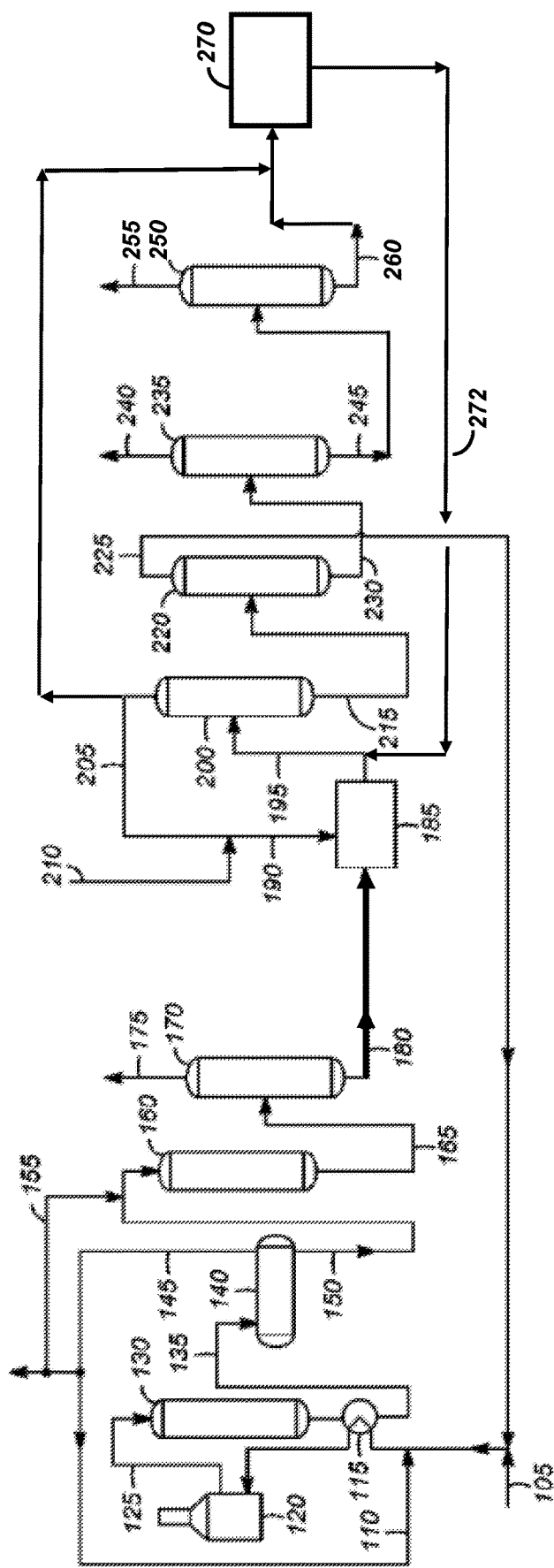
FIG. 1 shows a flow scheme to produce linear alkylbenzenes without an adsorbent unit to remove aromatic compounds but with units to remove heavy alkylated benzenes and a transalkylation unit to improve yield.

FIG. 1 shows a flow scheme that does not include an adsorbent unit to remove aromatic compounds due to the reduction in production of aromatics in this invention allowing for the elimination of this step of the prior art processes. A heavy alkylbenzene distillation column and transalkylation unit are added to increase production of monoalkylbenzenes. Integrated processes for producing LAB using solid alkylation catalysts have been developed. One example of an integrated process is shown in FIG. 1 which includes a dehydrogenation process, followed by a selective catalytic hydrogenation process, and an alkylation process. A paraffin feed 105 is mixed with hydrogen 110 and sent through heat exchanger 115 and charge heater 120. The heated stream 125 is sent to dehydrogenation zone 130. The dehydrogenation effluent 135 exchanges heat with the feed 105 and hydrogen 110 in heat exchanger 115. The dehydrogenation effluent 135 is then sent to a separator 140 and separated into a hydrogen gas stream 145 and liquid stream 150. The liquid stream 150 is mixed with hydrogen 155 and sent to a selective hydrogenation zone 160 where diolefins are hydrogenated. The effluent 165 from the selective hydrogenation reactor 160 is sent to a stripper 170 where light ends 175 are removed. The bottoms stream 180 from the stripper 170 is sent to an alkylation zone 185 where it is mixed with a benzene stream 190. The effluent 195 from the alkylation zone 185 is sent to a benzene distillation column 200. The benzene overhead stream 205 can be mixed with fresh benzene 210 to form the benzene stream 190. The bottoms stream 215 from the benzene column 200 is sent to a paraffin distillation column 220. The paraffin overhead stream 225 is mixed with paraffin feed 105 and sent to the dehydrogenation zone 130. The bottoms stream 230 from the paraffin column 220 is sent to an alkylbenzene distillation column 235 where it is separated into an overhead stream 240 containing the monoalkylbenzenes and a bottoms stream 245 containing heavy alkylbenzene (e.g., dialkylbenzene). The overhead stream 240 can be further processed, for example, in a finishing column (not shown), if desired.

The bottoms stream of heavy alkylbenzene can be further processed, for example as shown in a heavy alkylated benzene distillation column 250 to produce an overhead stream 255 of low-molecular weight heavy alkylbenzene and a bottoms stream 260 of a high molecular weight heavy alkylbenzene mixed with benzene which is sent to a transalkylation unit 270 to produce a transalkylation effluent stream comprising benzene, monoalkylbenzenes and unconverted high-molecular weight heavy alkylbenzene. Transalkylation effluent stream 272 is sent to the benzene distillation column 200 to recover the monoalkylbenzenes.

Figure 2:
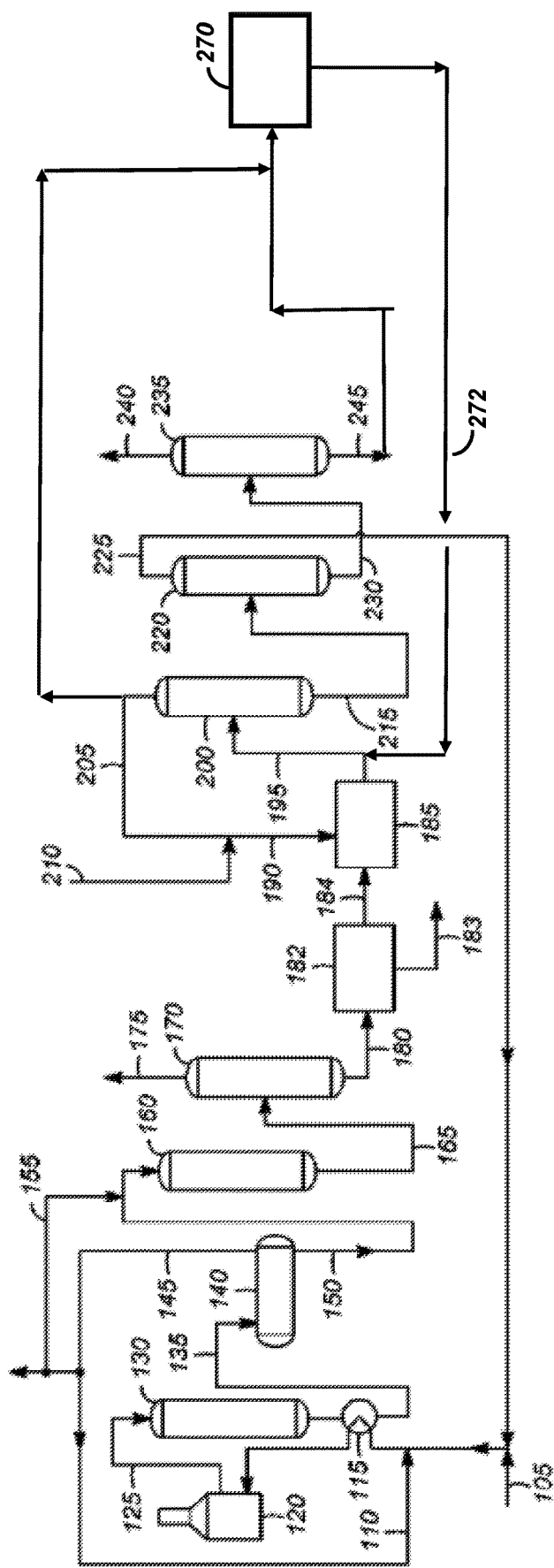
FIG. 2 shows a flow scheme to produce linear alkylbenzenes with the adsorbent unit to remove aromatic compounds and a transalkylation unit.

FIG. 2 shows a flow scheme similar to FIG. 1 except for including an adsorbent unit 182 for removing aromatic compounds 183 with the treated stream being sent to alkylation zone 185. A heavy alkylated benzene distillation column is not present in this particular flow scheme which otherwise with these exceptions functions the same as FIG. 1.

Figure 3:
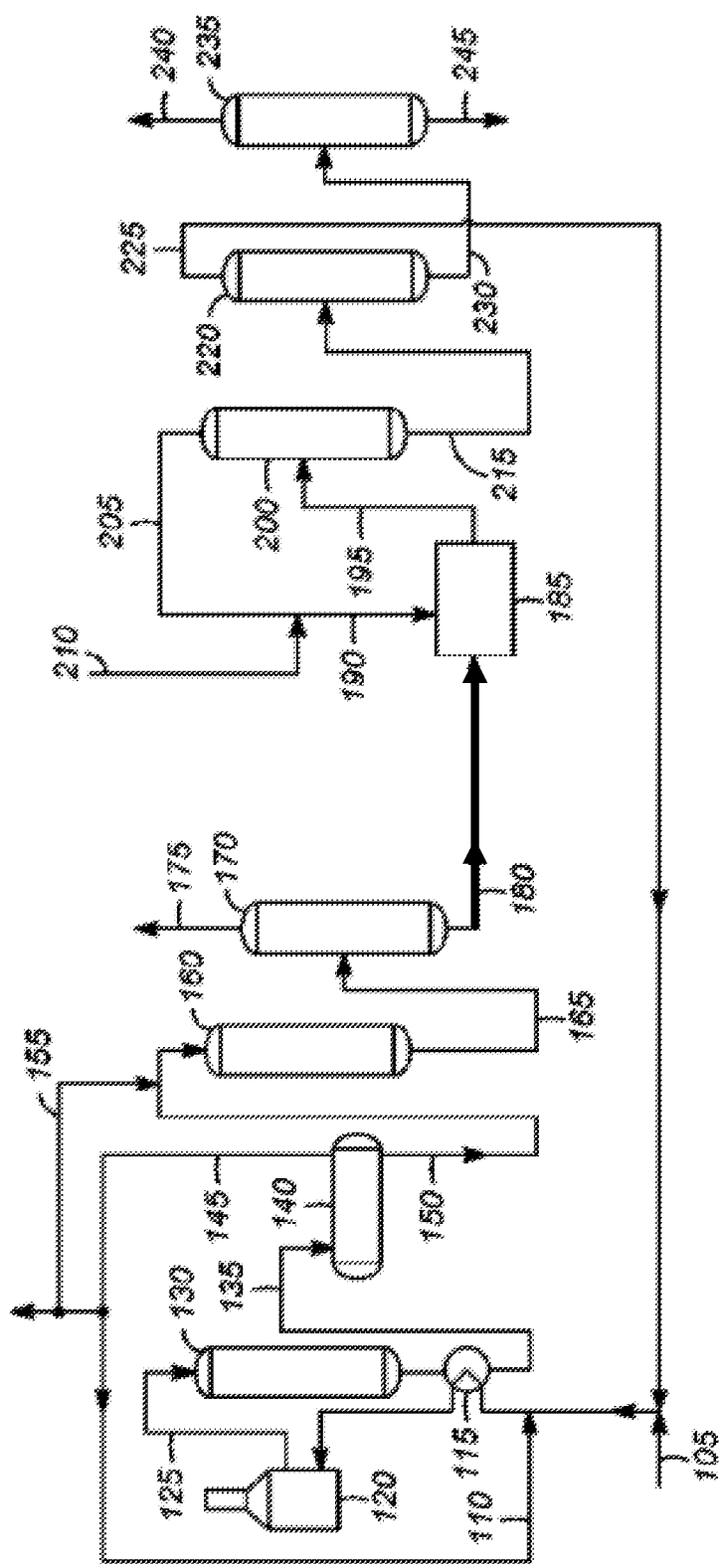
FIG. 3 shows a flow scheme to produce linear alkylbenzenes without the adsorbent unit to remove aromatic compounds.

FIG. 3 is also similar to FIGS. 1 and 2 except that in this flow scheme there is no adsorbent unit to remove aromatics, no heavy alkylated benzene distillation column, nor a transalkylation unit.

The aliphatic feedstock used in the alkylation processes of this invention contains aliphatic mono-olefin of 8 to 20, or 8 to 18, or 8 to 17 carbon atoms per molecule. The feed is typically limited to a range of 4 to 6 carbon numbers at any particular time. The aliphatic olefin is usually a mixture of olefins having different molecular weights. The olefin may be an alpha-olefin or comprise a mixture of olefin isomers. In most instances, the positioning of the olefinic bond in the molecule is not critical as most solid alkylation catalysts have been found to promote migration of the olefinic bond.

For commercial processes, other components may be present in the aliphatic feedstock with the olefin-containing aliphatic compound. These other components may comprise paraffins of for example, 9 to 17 carbon atoms per molecule which can act as heat sinks to maintain the desired temperature in the alkylation reaction zone as disclosed in U.S. Pat. No. 9,174,891 B2. However, such amounts of paraffin are not critical to the processes of this invention, and aliphatic feedstocks having an essential absence of paraffins can be used. If paraffins are not present, then another component that can act a heat sink and remains unreacted under the process conditions will need to be present to maintain the LAB linearity and 2-phenyl content, if that is needed for the particular application.

Hydrocarbons which can be dehydrogenated include hydrocarbons with 2 to 30 or more carbon atoms including normal paraffins, isoparaffins, alkylaromatics, naphthenes and olefins. A preferred group of hydrocarbons is the group of normal paraffins with 2 to about 30 carbon atoms. Especially preferred normal paraffins are those having 9 to 16 carbon atoms. Other especially preferred paraffins are monomethyl paraffins and dimethyl paraffins having from 9 to 16 carbon atoms. Each of the aforementioned hydrocarbons may be present alone or in a mixture with one or more of any of the other aforementioned hydrocarbons.

Dehydrogenation conditions include a temperature of from about 400° C. to about 900° C., a pressure of from about 1 to about 1013 kPa and a liquid hourly space velocity (LHSV) of from about 0.1 to about 100 hr$^{-1}$. As used herein, the abbreviation 'LHSV' means liquid hourly space velocity, which is defined as the volumetric flow rate of liquid per hour divided by the catalyst volume, where the liquid volume and the catalyst volume are in the same volumetric units. Generally, for paraffins, the lower the molecular weight, the higher is the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. These products include desirable olefins and undesirable light ends, aromatics, and others. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds. It is necessary to minimize the aromatic formation (or yield) in the dehydrogenation zone so that aromatic concentration does not accumulate in the recycled stream and does not increase the size (and cost) of the selective adsorbent and solvent to remove it.

A catalyst that has been found to be particularly efficient in producing a reduced amount of unwanted aromatic compounds is a catalyst composite with a layered composition comprising an inner core, an outer layer bonded to the inner core, the outer layer comprising one or more transition alumina with at least two diffraction angle peaks between 32.0° and 70.0° 2θ, wherein a first diffraction angle peak in that range is at 32.7±0.4° 2θ, a second diffraction angle peak is at 50.8±0.4° 2θ and having a thickness of less than about 100 microns and having uniformly dispersed thereon at least one platinum group metal and at least one promoter metal and having a concentration of the at least one platinum group metal of from about 0.00006 to 0.0005 gram of the platinum group metal on an elemental basis per meter square surface area of the outer layer, the layered composition further having dispersed thereon at least one modifier metal, the inner core and the outer refractory inorganic oxide being different materials.

The novel layered catalyst in this invention affords lower aromatic formation in the dehydrogenation zone. The combination of the platinum group concentration per meter square surface area of the outer layer of 0.00006 to 0.0005 and a composition including delta and/or theta alumina in the outer layer results in the formation of fewer aromatics. While the catalyst activity is still maintained by having substantial active metal platinum loading per cubic centimeter of catalyst or kilogram of the outer layer as described in U.S. Pat. No. 6,756,515 the lower aromatic formation is made possible by the delta and/or theta alumina outer layer with larger average pore size than that in gamma alumina layer. The aromatic products are formed by successive dehydrogenation of desirable olefins. Large alumina pores allow the olefins to diffuse out faster and consequently do not undergo undesirable dehydrogenation to aromatics.

The dehydrogenatable hydrocarbons may be admixed with a diluent material before, while or after being flowed to the dehydrogenation zone. The diluent material may be hydrogen, steam, methane, ethane, carbon dioxide, nitrogen, argon and the like or a mixture thereof. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, less than about 10000 weight ppm of the hydrocarbon feed stream, preferably less than 5000 weight ppm, more preferably less than 3000 weight ppm, and possibly even less than 1000 weight ppm. The process of this invention may be operated with no water or material which decomposes to form water added to the dehydrogenation zone.

In some embodiments, a multi-bed alkylation reaction zone and a split feed stream for controlling the 2-phenyl content in an alkylbenzene product stream are employed. This arrangement is described in U.S. Pat. No. 8,389,787. The split-bed design of U.S. Pat. No. 8,389,787 is optimized for feedstock utilization and energy consumption.

In one embodiment of the invention, the aromatic compound and the olefin are reacted under alkylation conditions in the presence of a solid alkylation catalyst. These alkylation conditions generally include a temperature in the range between about 80° C. and about 200° C., as discussed above. Typically, as the catalyst ages, the temperature of the alkylation is increased to maintain desired activity. The alkylation is an exothermic reaction, and thus in a substantially adiabatic reactor, the effluent is at a higher temperature than that of the feed. A substantially adiabatic reactor is one where the increase in temperature of the effluent over that of the feed accounts for at least about 75 percent of heat generated by the reactions in the reaction zone.

Typically, the temperature within a reaction zone is maintained within a suitable range by providing a large excess of aromatic compound to the reaction zone to absorb heat. Where the aliphatic feedstock contains paraffins, the paraffins also serve to absorb heat from the exothermic reactions. High exothermic temperatures during the alkylation can result in negative effects not only in terms of catalyst deactivation but also loss in linearity of the LAB due to increased olefin isomerization to non-linear olefins, which results in product quality degradation.

Since the alkylation is typically conducted in the presence of a liquid phase, and preferably in either an all-liquid phase or at supercritical conditions, pressures must be sufficient to maintain reactants in the liquid phase. The requisite pressure necessarily depends upon the olefin and temperature, but normally is in the range of about 1.300 to 7.000 MPa(g).

In some embodiments, alkylation of benzene by the olefins is conducted in a continuous manner using three or more catalyst beds in flow series. For purposes herein, a catalyst bed is termed a reaction zone whether in the same or a separate vessel from another bed. Each reaction zone has an inlet region and an outlet region. The reactants may be in admixture prior to entering the inlet region of the reaction zone, or they may be individually introduced and mixed in the reaction zone.

The catalyst may be used as a packed bed, a moving bed, or a slurry bed. The feed to the reaction zone may be passed either upflow or downflow, or even horizontally as in a radial bed reactor; however, the flows of the aromatic compound and olefin are co-current. In one desirable variant, olefin may be fed into several discrete points within the reaction zone. The feed mixture, that is, aromatic compound and aliphatic feedstock to a reaction zone, is often provided at an overall liquid hourly space velocity (overall LHSV) between about 0.3 and about 6 or 10 hr$^{-1}$, and most frequently between about 0.4 and 6 hr$^{-1}$ depending upon, e.g., alkylation temperature and the activity of the catalyst. The overall LHSV is determined from the LHSV's of each of the beds. The reciprocal of the overall LHSV is the sum of the reciprocals of the LHSV of each of the beds in series.

It is usually desired that sufficient residence time in the reaction zone be used such that at least about 90, or at least about 95, or at least about 98, and often at least about 99.5, mass percent of the olefin fed to a reaction zone is reacted in that reaction zone.

Any suitable solid alkylation catalyst may be used in the present invention, provided that the requirements for conversion, selectivity, and activity are met. Typically, the catalysts are acidic. Preferred alkylation catalysts comprise zeolites having a zeolite framework type selected from the group consisting of FAU, MOR, MTW, and NES. Suitable zeolites include mordenite, ZSM-4, ZSM-12, ZSM-20, ZSM-38, offretite, gmelinite, beta, NU-87, UZM-8, MCM-22, MCM-36, MCM-49, zeolite Y, zeolite X, and gottardite. The MOR, MWW, FAU, NES, and other zeolite framework types are described in Ch. Baerlocher, W. M. Meier and D. H. Olson, "Atlas of Zeolite Framework Types," 5th Ed., Elsevier: Amsterdam, 2001, herein incorporated by reference. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1.

Newer alkylation catalysts can also be used in this process. For example, one such catalyst comprises a mixture of two types of zeolitic materials, where the zeolites are mixed and produced to have two zeolites within a single catal'st pellet. With the new catalysts, the first zeolite is also characterized by its acidity, wherein the acidity is characterized by having less than 70% of NH$_3$ desorption off the zeolite at temperatures greater than 400° C. The NH$_3$-TPD experimental procedure comprises calibration of the NH$_3$-TPD system with 5 injections of 0.2 cc pulses of NH$_3$ at 2 minute intervals into a flow of UHP grade helium at 40 cc/minute. The data collected from the Thermal Conductivity Detector is integrated and used to calibrate the detector response to a known quantity of NH$_3$. An equilibrated sample is weighed at approximately 250 mg and placed in the reactor. The sample is pretreated in a flow of 20% O$_2$/He UHP grade at a rate of 100 cc/minute and with a temperature ramp of 10° C./minute up to a maximum temperature of 650° C. The sample is held at this temperature for one hour, then purged with UHP grade helium for 15 minutes and cooled to the saturation temperature. The pretreatment is for removal of water and residual contaminants. The sample is saturated with anhydrous NH$_3$ at 150° C. using multiple pulses of NH$_3$ injected into He flowing at 40 cc/min. The minimum quantity of NH$_3$ used to saturate the sample is 50 cc. The excess ammonia is purged from the sample in flowing (40 cc/min) UHP grade helium for about 8 hours. The NH$_3$ is desorbed from the sample in a flow (40 cc/min) of UHP grade helium with a temperature ramp of 10° C./minute to a final temperature of about 605° C. All gases have been purified using appropriate gas purifiers. The NH$_3$ desorbed is detected with a Thermal Conductivity Detector. The detector response is converted to moles of NH$_3$ using the detector response obtained at the beginning of the experiment. The integrated results are reported by integration of the temperature range of interest and reported as mmoles NH$_3$/g sample. An example of the first zeolite is UZM-8.

The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles. An example of the second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage. The reduced acidity and reduced space significantly suppress the isomerization and cracking pathways, while leaving the primary alkylation reaction unaffected. This decreases the undesired side reactions that reduce the amount and quality of the LAB product. This is contrary to what one would expect, as it has been found that incorporating or leaving some alkali or alkaline earth cations in the catalyst significantly improves the catalyst performance. This is especially true with respect to the performance around the linearity of the alkylbenzene, and the retention of linearity as the operating temperatures are increased. Normally, the alkali or alkaline earth cations are removed because without the rare earth exchange, the alkali or alkaline earth cations are detrimental to the catalyst life and regenerability.

The alkylation reaction zone may contain at least 2, or at least 3, and most frequently between about 3 and 10, reaction zones in series to which a portion of the aliphatic feedstock is fed. Often a trim alkylation reaction zone follows the series to react residual olefin in the effluent from the last reaction zone in series. The reaction zones may be in a common vessel or in separate vessels. The reaction zones may be the same or different sizes Additional reaction zones may be used in parallel.

In common commercial configurations for alkylbenzene, the refining assembly comprises a distillation assembly that recovers essentially all the benzene from the alkylation effluent and provides a relatively pure benzene stream as overhead. The bottoms stream from this distillation assembly would then be passed to a distillation assembly to separate as the overhead, paraffins and unreacted olefins, and the bottoms from this second distillation assembly would be fed to a heavies distillation assembly where the alkylbenzene product is contained in the overhead. If desired, a finishing column may be used to further purify the alkylbenzene, especially after a clay treatment to remove color formers.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The following examples are presented in illustration of this invention and are not intended as undue limitations on the generally broad scope of the invention as set out in the appended claims.

Example 1

Alumina spheres were prepared by the well-known oil drop method, which is described in U.S. Pat. No. 2,620,314. This process involves forming an aluminum hydrosol by dissolving aluminum in hydrochloric acid. Hexamethylene tetraamine was added to the sol to gel the sol into spheres when dispersed as droplets into an oil bath maintained at about 93° C. The droplets remained in the oil bath until they set and formed hydrogel spheres. After the spheres were removed from the hot oil, they were pressure-aged at about 135° C. and washed with dilute ammonium hydroxide solution, dried at about 110° C. and calcined at about 650° C. for about 2 hours to give gamma alumina spheres. The calcined alumina was then crushed into a fine powder having a particle size of less than 200 microns.

Next, a slurry was prepared by mixing pseudoboehmite and deionized water and agitated to uniformly distribute the tin component. To this mixture there were added the above prepared alumina powder and a 50% aqueous solution of tin(IV) chloride, and the slurry was ball milled for approximately 240 minutes thereby reducing the maximum particle size to less than 50 microns. This slurry was sprayed onto cordierite cores having an average diameter of about 1.6 mm by using a granulating and coating apparatus to give an outer layer of about 25 or 65 microns. At the end of the process, some of the slurry was left which did not coat the cores. This layered spherical support was calcined at about 600° C. to 900° C. in order to convert the pseudoboehmite and gamma alumina in the Outer layer into delta alumina and convert the tin chloride to tin oxide.

The calcined layered support was impregnated with lithium and platinum using a rotary impregnator by contacting the support with an aqueous solution (1:1 solution: support Volume ratio) containing lithium chloride and chloroplatinic acid based on Support weight. The impregnated composite was heated using a rotary impregnator until no solution remained, dried at about 315° C. and calcined at about 540° C. and reduced in hydrogen at about 500° C. The resulting catalyst prepared in this example contained 0.1-0.2 wt-% platinum, 0.1-0.2 wt-% tin, and 0.1-0.2 wt-% lithium with respect to the entire catalyst. These catalysts were identified as Catalyst A, B, C, and D. The properties of catalyst A, B, C, and D are summarized in Table 1.

TABLE 1

| Catalyst | Catalyst A | Catalyst B | Catalyst C | Catalyst D |
|---|---|---|---|---|
| Pt wt. % | 0.1-0.2 | 0.1-0.2 | 0.1-0.2 | 0.1-0.2 |
| Sn wt. % | 0.1-0.2 | 0.1-0.2 | 0.1-0.2 | 0.1-0.2 |
| Li wt. % | 0.1-0.2 | 0.1-0.2 | 0.1-0.2 | 0.1-0.2 |
| Layer thickness (μm) | 65 | 25 | 65 | 25 |
| Alumina calcination temp (C.) | 600 | 600 | 900 | 900 |
| Alumina in layer | Gamma | Gamma | Delta and/or theta | Delta and/or theta |
| Alumina layer surface area ($m^2/g$) | 203 | 227 | 133 | 156 |
| Grams of Pt in alumina layer/layer surface area ($g/m^2$) | 0.000041 | 0.000093 | 0.000062 | 0.000135 |
| Mole of Pt in alumina layer/kg of layer (mol/kg) | 0.04 | 0.11 | 0.04 | 0.11 |
| Grams of Platinum in cubic centimeter of catalyst ($g/cm^3$) | 0.0012 | 0.0012 | 0.0012 | 0.0012 |

Example 2

Catalyst A, B, C and D from Example 1 were tested for dehydrogenation activity in a laboratory scale plant. In a 1.27 cm reactor, 5 cc of catalyst was placed and a hydrocarbon feed composed of 8.8-9.3 wt-% n-$C_{10}$, 40.0-41.8 wt-% n-$C_{11}$, 38.6 wt-% n-$C_{12}$, 8.6-10.8 wt-% n-$C_{13}$, 0.3-0.8 wt-% n-$C_{14}$ and 1-1.4 wt-% non-normals was flowed over the catalyst under a pressure of 138 kPa (or 20 psig), a hydrocarbon molar ratio of 4:1, and a liquid hourly space velocity (LHSV) of 28 $hr^{-1}$. The total normal olefin concentration in the product (% TNO) was maintained at 10 wt.-% by adjusting reactor temperature.

Hydrogen and hydrocarbon feed were combined upstream of the reactor to form a combined feed, and the combined feed was vaporized prior to entering the reactor. In this example, the catalyst was tested at water concentrations of 2000 wt-ppm based on the weight of the hydrocarbon in the combined feed. The results of the product liquids collected at 48-hour on stream for the four listed catalysts are presented in the Table 2.

The feed and product streams were analyzed for aromatic content by utilizing a backflush on a high-performance liquid chromatography (HPLC) system using n-hexane solvent as the mobile phase and a refractive index detector.

Normal-paraffin conversion %=(normal paraffin in the feed−normal paraffin in product)×100%/ Normal paraffin in the feed. Aromatic selectivity %=(aromatic in the product−aromatic in the feed)×100%/Normal-paraffin conversion.

Even though catalyst B showed lower aromatic selectivity than catalyst A, its aromatic selectivity was still higher than Catalyst C and D. Thus, the combination of one or more transition alumina phase (delta and/or theta alumina) in the layer and high Pt density (grams of Pt in alumina layer/layer surface area ($g/m^2$)) enabled the lowest aromatic formation.

TABLE 2

| Sample ID | Aromatic selectivity (%) |
|---|---|
| Catalyst A | 2.18 |
| Catalyst B | 1.80 |
| Catalyst C | 1.60 |
| Catalyst D | 1.62 |

Example 3

Figure 4:
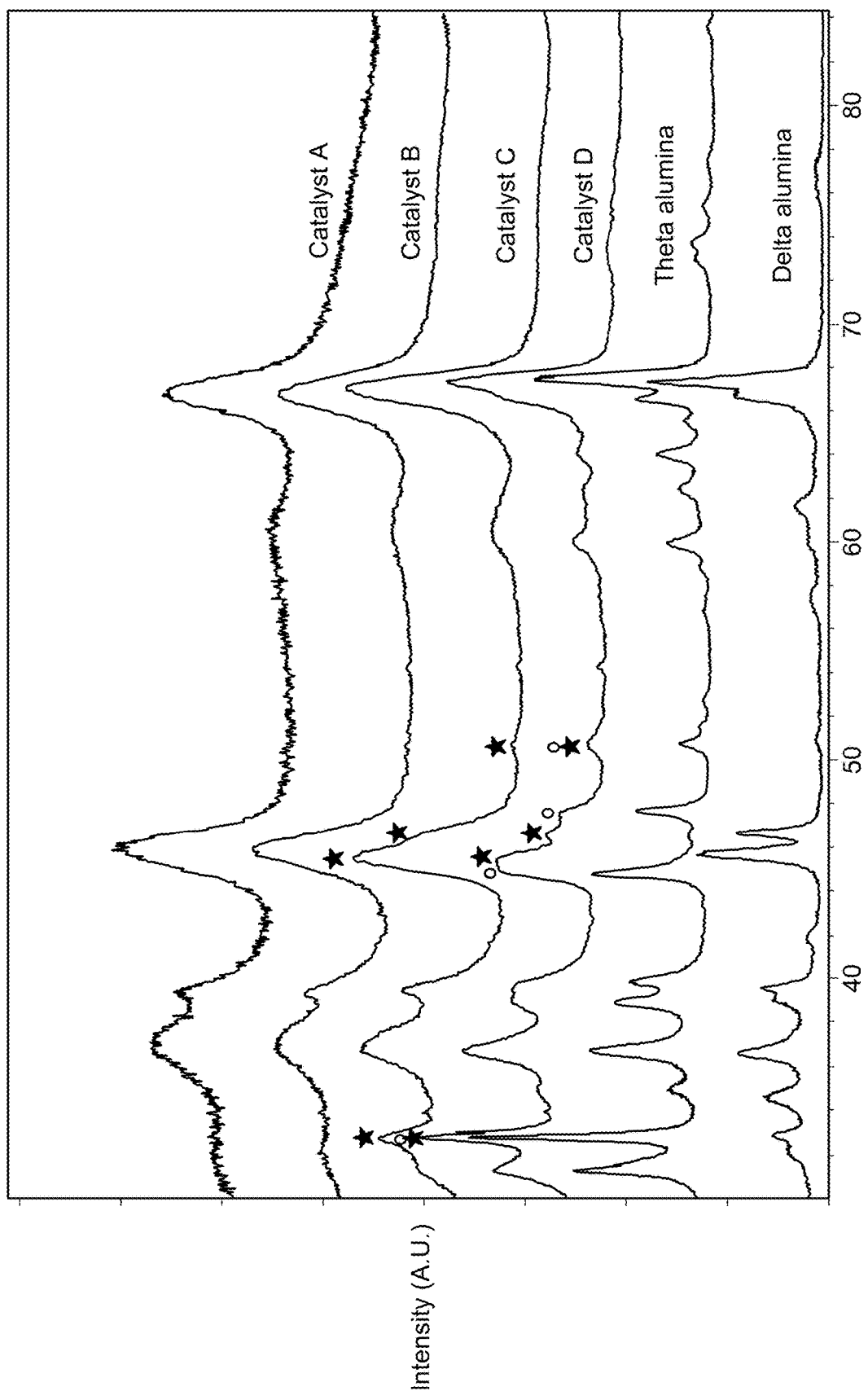
FIG. 4 shows X-ray diffraction patterns for the outer layer of alumina in the catalyst.

The alumina layers of the four catalysts A, B, C, and D of the present disclosure were analyzed by X-ray Diffraction to investigate for the presence of delta or theta alumina as shown in FIG. 4. An attempt was made to remove only the outer layer material by placing 1 cc of calcined base into small milling vessel with no milling media. Samples were abraded for various amounts of time depending on how quickly powder from the outer layer was generated. The powders from the four catalytic composites were labeled as sample A, B, C, and D.

The X-ray patterns of sample A, B, C, and D were obtained using standard X-ray powder diffraction techniques. The radiation source was a high-intensity X-ray tube operated at 40 kV and 44 mA. The diffraction pattern from the copper K-alpha radiation was obtained by appropriate computer-based techniques. Flat compressed powder samples were continuously scanned at 8° to 90° 2θ. Interplanar spacings (d) in Angstrom units were obtained from the position of the diffraction peaks expressed as 2θ, where 2θ is the Bragg angle as observed from digitized data. As will be understood by those skilled in the art, the determination of the diffraction angles (2θ) is subject to both human and mechanical error, which in combination can impose an uncertainty of about 0.4° 2θ on each reported value of 2θ.

The outer layers in the catalyst C and D comprise essentially delta and/or theta alumina. Their X-ray diffraction patterns contain at least two diffraction angle peaks between 32.0° and 70.0° 2θ, wherein a first diffraction angle peak in that range is at 32.7±0.4° 2θ, a second diffraction angle peak is at 50.8±0.4° 2θ. In addition, the X-ray diffraction patterns have at least 2 peaks and/or shoulders between about 43±0.4° to about 49±0.4° 2θ.

Example 4

The ratio of fresh feed/LAB=flow rate of stream 105/flow rate of stream 240 in the flow process schemes in FIGS. 1, 2, and 3. The lower ratio is preferred due to lower feed consumption for a given LAB production rate. The fresh feed/LAB ratios calculated for FIGS. 1, 2, and 3 for selected dehydrogenation zone and alkylation catalysts are reported in Table 3. The molecular weight (MW) of paraffin feed used in these calculations ranges from 155 to 165 g/mol.

The novel layered catalyst in this invention affords lower aromatic formation in the dehydrogenation zone. A portion of these undesirable aromatics in the dehydrogenation zone effluent reacts in the alkylation unit to form low molecular weight heavy alkylated benzene further increasing the fresh feed/LAB ratio and thus increasing the cash cost of production. The combination of the layered catalyst and the FIG. 1 flow scheme has approximately equivalent feed efficiency to current state-of-the-art technology with HF while eliminating the safety risks associated with HF and the need for additional processing steps to remove undesirable aromatics prior to alkylation by a solid acid catalyst.

TABLE 3

| Flow scheme | Dehydrogenation Zone Catalyst | Alkylation Catalyst | Fresh feed/LAB |
|---|---|---|---|
| FIG. 1 | Catalyst A | SBA | 0.759 |
| FIG. 1 | Catalyst C | SBA | 0.753 |
| FIG. 2 | Catalyst A | SBA | 0.744 |
| FIG. 2 | Catalyst C | SBA | 0.739 |
| FIG. 3. | Catalyst A | HF | 0.755 |
| FIG. 3. | Catalyst C | HF | 0.749 |

SPECIFIC EMBODIMENTS

While the following is described in conjunction with specific embodiments, it will be understood that this description is intended to illustrate and not limit the scope of the preceding description and the appended claims.

A first embodiment of the invention is a process for producing monoalkylbenzenes comprising passing C9-C14 paraffinic stream and a hereinafter derived paraffinic recycle stream to a dehydrogenation zone maintained at dehydrogenation conditions containing a dehydrogenation catalyst to produce an effluent stream comprising light hydrocarbon, hydrogen, feed paraffin hydrocarbons, corresponding monoolefinic and diolefinic hydrocarbons to the feed paraffin hydrocarbons and C9-C14 alkylaromatics, wherein the effluent stream comprises less than 1.4 wt % of the C9-C14 alkylaromatics wherein the dehydrogenation zone catalyst comprises a layered catalyst composition comprising an inner core, an outer layer bonded to the inner core, the outer layer comprising an outer refractory inorganic oxide with a layer thickness less than about 100 microns having uniformly dispersed thereon at least one platinum group metal and at least one promoter metal; sending at least a portion of the effluent stream to a selective hydrogenation reactor to convert the diolefinic hydrocarbons to monoolefinic hydrocarbons and producing a treated effluent stream; sending the treated effluent stream to an alkylation zone; sending an aromatics stream comprising benzene to the alkylation zone operated at alkylation conditions to generate a process stream comprising paraffins, benzene, monoalkylbenzenes and heavy alkylbenzenes (HAB); separating the process stream, in a first separation unit, into a first stream comprising benzene, and a second stream comprising alkylbenzenes and paraffins; passing the second stream to a second separation unit to generate a third stream comprising paraffins, which is recycled back to the dehydrogenation zone, and a fourth stream comprising alkylbenzenes; and passing the fourth stream to a third separation unit to generate a fifth stream comprising monoalkylated benzene and a sixth stream comprising heavy alkylbenzenes (HAB). An embodiment of the invention is one, any or all of prior embodiments in this paragraph up through the first embodiment in this paragraph wherein the ratio of mass of C9-C14 paraffinic stream to mass of the fifth stream is less than 0.75. An embodiment of the invention is one, any or all of prior embodiments in this paragraph up through the first embodiment in this paragraph wherein the ratio of mass of C9-C14 paraffinic stream to mass of the fifth stream is less than 0.74. An embodiment of the invention is one, any or all of prior embodiments in this paragraph up through the first embodiment in this paragraph wherein the ratio of mass of C9-C14 paraffinic stream to mass of the fifth stream is less than 0.73. An embodiment of the invention is one, any or all of prior embodiments in this paragraph up through the first embodiment in this paragraph wherein the alkylation zone comprises a catalyst selected from mordenite, ZSM-4, ZSM-12, ZSM-20, ZSM-38, offretite, gmelinite, beta, NU-87, UZM-8, MCM-22, MCM-36, MCM-49, zeolite Y, zeolite X, gottardite, MOR, MWW, FAU, RE-Y, NES, fluorided-ASA, or combinations thereof. An embodiment of the invention is one, any or all of prior embodiments in this paragraph up through the first embodiment in this paragraph wherein the alkylation zone comprises a hydrofluoric acid catalyst. An embodiment of the invention is one, any or all of prior embodiments in this paragraph up through the first embodiment in this paragraph wherein the dehydrogenation zone catalyst comprises a layered catalyst composition with an outer layer comprising one or more transition alumina with at least at two diffraction angle peaks between 32.0° and 70.0° 2θ, wherein a first diffraction angle peak in that range is at 32.7±0.4° 2θ, a second diffraction angle peak is at 50.8±0.4° 2θ. An embodiment of the invention is one, any or all of prior embodiments in this paragraph up through the first embodiment in this paragraph wherein the dehydrogenation zone catalyst comprises a layered catalyst composition with an outer layer comprising one or more transition alumina with at least 2 diffraction angle peaks and/or shoulders between about 43±0.4° to about 49±0.4° 2θ. An embodiment of the invention is one, any or all of prior embodiments in this paragraph up through the first embodiment in this paragraph wherein the dehydrogenation zone catalyst comprises a layered catalyst composition having a concentration of the at least one platinum group metal of from about 0.00006 to 0.0005 gram of the platinum group metal on an elemental basis per meter square surface area of the outer layer. An embodiment of the invention is one, any or all of prior embodiments in this paragraph up through the first embodiment in this paragraph wherein the dehydrogenation zone effluent stream comprises less than 1.2 wt. % of the C9-C14 alkylaromatics. An embodiment of the invention is one, any or all of prior embodiments in this paragraph up through the first embodiment in this paragraph wherein the dehydrogenation zone effluent stream comprises less than 1.0 wt. % of the C9-C14 alkylaromatics. An embodiment of the invention is one, any or all of prior embodiments in this paragraph up through the first embodiment in this paragraph further comprising passing the fifth stream to a sulfonation unit to convert monoalkylated benzene to monoalkylated benzene sulfonate. An embodiment of the invention is one, any or all of prior embodiments in this paragraph up through the first embodiment in this paragraph further comprising sending the treated effluent stream to an aromatic separation zone to remove at least a portion of the C9-C14 alkylaromatics and then sending a remaining portion of the treated effluent stream to the alkylation zone. An embodiment of the invention is one, any or all of prior embodiments in this paragraph up through the first embodiment in this paragraph further comprising passing the sixth stream to a fourth separation unit to generate a seventh stream comprising low-molecular weight HAB, and an eighth stream comprising high-molecular weight HAB. An embodiment of the invention is one, any or all of prior embodiments in this paragraph up through the first embodiment in this paragraph further comprising passing the eighth stream to a transalkylation zone; passing a benzene stream to the transalkylation zone operated at transalkylation conditions to generate a transalkylation effluent stream comprising monoalkylbenzenes; and passing the transalkylation effluent stream to the first separation unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing monoalkylbenzenes comprising a. passing C9-C14 paraffinic stream and a hereinafter derived paraffinic recycle stream to a dehydrogenation zone maintained at dehydrogenation conditions containing a dehydrogenation catalyst to produce an effluent stream comprising light hydrocarbon, hydrogen, feed paraffin hydrocarbons, corresponding monoolefinic and diolefinic hydrocarbons to said feed paraffin hydrocarbons and C9-C14 alkylaromatics, wherein said effluent stream comprises less than 1.4 wt % of said C9-C14 alkylaromatics wherein said dehydrogenation zone catalyst comprises a layered catalyst composition comprising an inner core, an outer layer bonded to said inner core, the outer layer comprising an outer refractory inorganic oxide with a layer thickness less than about 100 microns having uniformly dispersed thereon at least one platinum group metal and at least one promoter metal;

b. sending at least a portion of said effluent stream to a selective hydrogenation reactor to convert said diolefinic hydrocarbons to monoolefinic hydrocarbons and producing a treated effluent stream;

c. sending said treated effluent stream to an alkylation zone;

d. sending an aromatics stream comprising benzene to said alkylation zone operated at alkylation conditions to generate a process stream comprising paraffins, benzene, monoalkylbenzenes and heavy alkylbenzenes (HAB);

e. separating the process stream, in a first separation unit, into a first stream comprising benzene, and a second stream comprising alkylbenzenes and paraffins;

f. passing the second stream to a second separation unit to generate a third stream comprising paraffins, which is recycled back to the dehydrogenation zone, and a fourth stream comprising alkylbenzenes; and g. passing the fourth stream to a third separation unit to generate a fifth stream comprising monoalkylated benzene and a sixth stream comprising heavy alkylbenzenes (HAB).

2. The process of claim 1 wherein the ratio of mass of C9-C14 paraffinic stream to mass of the fifth stream is less than 0.75.

3. The process of claim 1 wherein the ratio of mass of C9-C14 paraffinic stream to mass of the fifth stream is less than 0.74.

4. The process of claim 1 wherein the ratio of mass of C9-C14 paraffinic stream to mass of the fifth stream is less than 0.73.

5. The process of claim 1 wherein said alkylation zone comprises a catalyst selected from mordenite, ZSM-4, ZSM-12, ZSM-20, ZSM-38, offretite, gmelinite, beta, NU-87, UZM-8, MCM-22, MCM-36, MCM-49, zeolite Y, zeolite X, gottardite, MOR, MWW, FAU, RE-Y, NES, fluorided-ASA, or combinations thereof.

6. The process of claim 1 wherein said alkylation zone comprises a hydrofluoric acid catalyst.

7. The process of claim 1 wherein said dehydrogenation zone catalyst comprises a layered catalyst composition with an outer layer comprising one or more transition alumina with at least at two diffraction angle peaks between 32.0° and 70.0° 2θ, wherein a first diffraction angle peak in that range is at 32.7±0.4° 2θ, a second diffraction angle peak is at 50.8±0.4° 2θ.

8. The process of claim 1 wherein said dehydrogenation zone catalyst comprises a layered catalyst composition with an outer layer comprising one or more transition alumina with at least 2 diffraction angle peaks and/or shoulders between about 43±0.4° to about 49±0.4° 2θ.

9. The process of claim 1 wherein said dehydrogenation zone catalyst comprises a layered catalyst composition having a concentration of the at least one platinum group metal of from about 0.00006 to 0.0005 gram of the platinum group metal on an elemental basis per meter square surface area of the outer layer.

10. The process of claim 1 wherein the dehydrogenation zone effluent stream comprises less than 1.2 wt. % of said C9-C14 alkylaromatics.

11. The process of claim 1 wherein the dehydrogenation zone effluent stream comprises less than 1.0 wt. % of said C9-C14 alkylaromatics.

12. The process of claim 1 further comprising passing the fifth stream to a sulfonation unit to convert monoalkylated benzene to monoalkylated benzene sulfonate.

13. The process of claim 1 further comprising sending said treated effluent stream to an aromatic separation zone to remove at least a portion of said C9-C14 alkylaromatics and then sending a remaining portion of said treated effluent stream to said alkylation zone.

14. The process of claim 1 further comprising passing the sixth stream to a fourth separation unit to generate a seventh stream comprising low-molecular weight HAB, and an eighth stream comprising high-molecular weight HAB.

15. The process of claim 1 further comprising passing the eighth stream to a transalkylation zone; passing a benzene stream to the transalkylation zone operated at transalkylation conditions to generate a transalkylation effluent stream comprising monoalkylbenzenes; and passing the transalkylation effluent stream to the first separation unit.

\* \* \* \* \*